(12) United States Patent
Bauer et al.

(10) Patent No.: US 10,267,884 B2
(45) Date of Patent: Apr. 23, 2019

(54) METHOD FOR CREATING A MOTION CORRECTION FOR PET DATA, A METHOD FOR CREATING PET IMAGES AS WELL AS A CORRESPONDINGLY EMBODIED MR SYSTEM AND PET SYSTEM

(71) Applicant: Siemens Aktiengesellschaft, Munich (DE)

(72) Inventors: Simon Bauer, Baunach (DE); Isabel Dregely, Munich (DE); Sebastian Fürst, Munich (DE); Robert Grimm, Nuremberg (DE); Berthold Kiefer, Erlangen (DE); Marcel Dominik Nickel, Herzogenaurach (DE)

(73) Assignee: SIEMENS AKTIENGESELLCHAFT, Munich (DE)

( * ) Notice: Subject to any disclaimer, the term of this patent is extended or adjusted under 35 U.S.C. 154(b) by 1010 days.

(21) Appl. No.: 14/225,824

(22) Filed: Mar. 26, 2014

(65) Prior Publication Data
US 2014/0296698 A1    Oct. 2, 2014

(30) Foreign Application Priority Data

Mar. 28, 2013    (DE) .................. 10 2013 205 576

(51) Int. Cl.
*A61B 5/055* (2006.01)
*G01R 33/565* (2006.01)
(Continued)

(52) U.S. Cl.
CPC ........ *G01R 33/56509* (2013.01); *A61B 5/055* (2013.01); *A61B 6/037* (2013.01);
(Continued)

(58) Field of Classification Search
CPC ... A61B 2576/00; A61B 5/0035; A61B 5/055; A61B 6/037; A61B 6/5247; A61B 6/5264; G01R 33/481; G01R 33/56509
See application file for complete search history.

(56) References Cited

U.S. PATENT DOCUMENTS

2008/0135769 A1*  6/2008  Rosen .................. G01T 1/1603
                                                                    250/363.09
2008/0287772 A1    11/2008  Declerck
(Continued)

FOREIGN PATENT DOCUMENTS

DE      102009017439 A1    10/2010
WO      WO 2008/132659    * 11/2008

OTHER PUBLICATIONS

Tsoumpas, Charalampos et al.: "Simultaneous PET-MR acquisition and MR-derived motion fields for correction of non-rigid motion in PET"; in: Ann Nucl Med.; 2010; vol. 24: pp. 745-750; DOI 10.1007/s12149-010-0418-2.
(Continued)

*Primary Examiner* — Ruth S Smith
(74) *Attorney, Agent, or Firm* — Harness, Dickey & Pierce, P.L.C.

(57) ABSTRACT

A method is disclosed for creating a motion correction for PET data acquired by a PET system from a volume segment of an examination object. The method includes acquisition of MR data within the volume segment by the magnetic resonance system; and determination of a motion model of a motion within the volume segment as a function of the MR data. The motion model, as a function of a respective motion state of the motion, provides a correction specification for PET data which is acquired during this motion state. During acquisition of the MR data, specific MR data is acquired in the center of the k-space or of a straight-line segment which passes through the center of the k-space. The MR data determined is converted by a mathematical function into one value, as a function of which the respective motion state is determined.

12 Claims, 3 Drawing Sheets

(51) Int. Cl.
*G01R 33/48* (2006.01)
*A61B 6/00* (2006.01)
*A61B 6/03* (2006.01)
*A61B 5/00* (2006.01)

(52) U.S. Cl.
CPC .......... *A61B 6/5247* (2013.01); *A61B 6/5264* (2013.01); *G01R 33/481* (2013.01); *A61B 5/0035* (2013.01); *A61B 2576/00* (2013.01)

(56) References Cited

U.S. PATENT DOCUMENTS

2010/0106004 A1* 4/2010 Harvey ............ G01R 33/56509
600/411
2010/0268063 A1 10/2010 Schmidt
2010/0290683 A1 11/2010 Demeester

OTHER PUBLICATIONS

Chun, Se Young et al.: "MRI-Based Nonrigid Motion Correction in Simultaneous PET/MRI"; in: Journal of Nuclear Medicine; 2012: vol. 53; pp. 1-8; DOI 10.2967/jnumed.111.092353.

Buerger, C. et al.: "Nonrigid Motion Modeling of the Liver From 3-D Undersampled Self-Gated Golden-Radial Phase Encoded MRI"; in: IEEE Transactions on Medical Imaging; 2012; vol. 31, No. 3; pp. 805-815; ISSN: 0278-0062.

Würslin, Christian et al.: "MR-based Compensation of Respiratory Motion Artifacts of In-Vivo PET Images Acquired on a Simultaneous Whole-Body MR/PET System"; in: Proc. Intl. Soc. Mag. Reson. Med.; 2012; vol. 20; p. 147.

* cited by examiner

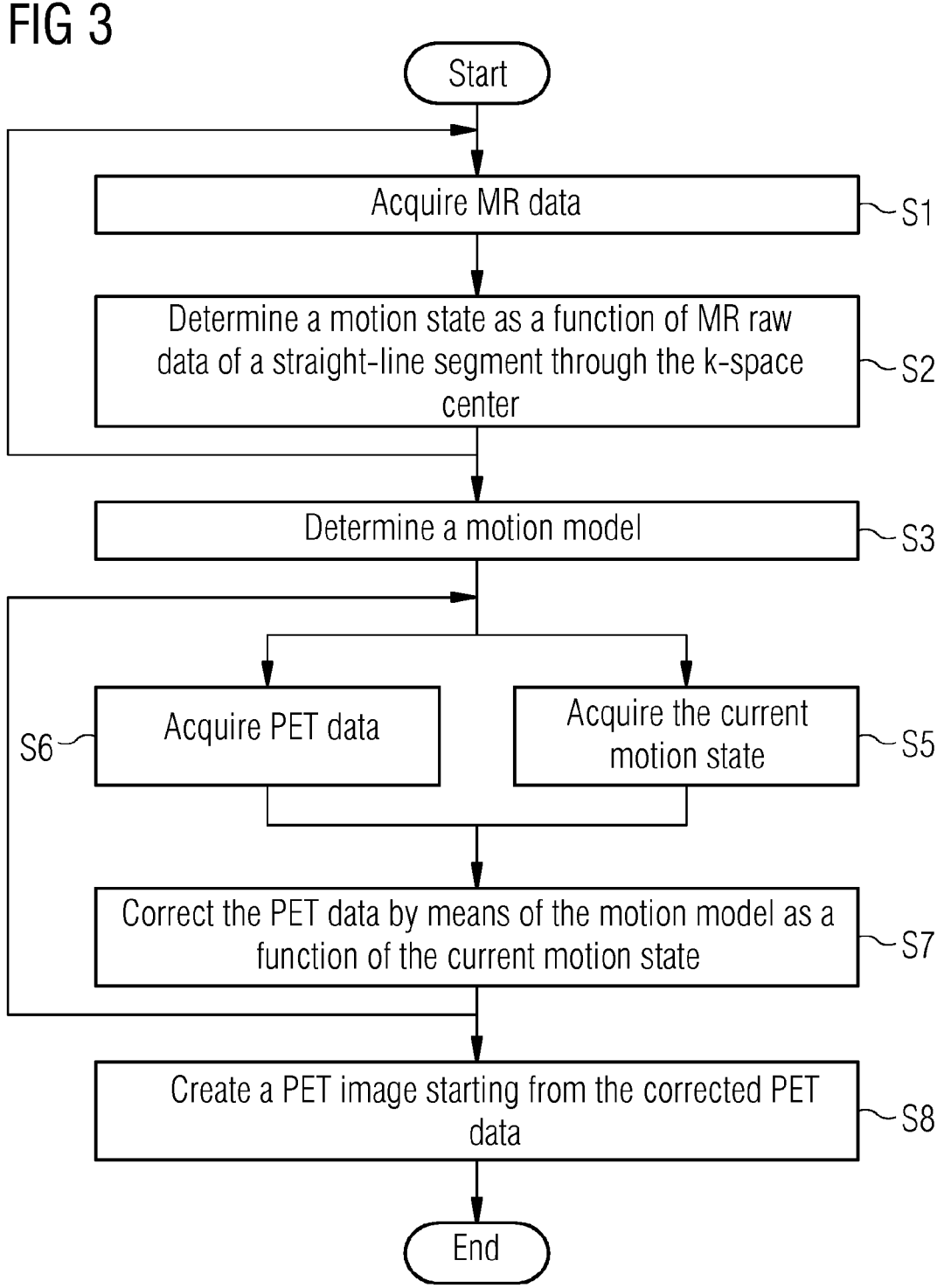

METHOD FOR CREATING A MOTION CORRECTION FOR PET DATA, A METHOD FOR CREATING PET IMAGES AS WELL AS A CORRESPONDINGLY EMBODIED MR SYSTEM AND PET SYSTEM

PRIORITY STATEMENT

The present application hereby claims priority under 35 U.S.C. § 119 to German patent application number DE 102013205576.5 filed Mar. 28, 2013, the entire contents of which are hereby incorporated herein by reference.

FIELD

At least one embodiment of the present invention generally relates to a method for creating a motion correction in relation to PET data acquired by way of a PET system and/or to a method for creating PET images by way of this motion correction, and/or a correspondingly embodied MR system and/or a correspondingly embodied PET system.

BACKGROUND

In accordance with the prior art, the acquisition of PET data of the abdomen occurs, as result of a measuring time of several minutes, with the patient breathing freely. It is therefore usual in accordance with the prior art, both for the computation of the attenuation map and also for the reconstruction of PET images from the PET data, to undertake a motion correction (especially of the respiration motion). The motion correction enables motion artifacts (unsharp and falsified intensity values) in the PET images to be at least reduced, whereby a diagnosis by the doctor on the basis of the PET images is advantageously not adversely affected by motion artifacts.

In "Simultaneous PET-MR acquisition and MR-derived motion fields for correction of non-rigid motion in PET", C. Tsoumpas et al., Ann Nucl Med (2010) 24, pages 745-750, a motion correction during creation of PET images is described, in that MR data is acquired simultaneously with the PET data in order to undertake the motion correction by means of this MR data.

SUMMARY

At least one embodiment of the present invention is directed to simplifying motion correction during acquisition of PET data.

In accordance with at least one embodiment of the invention, a method is disclosed for creating a motion correction for PET data. In at least one embodiment of the invention, a method is disclosed for creating PET images. In at least one embodiment of the invention, a magnetic resonance system is disclosed. In at least one embodiment of the invention, a PET system is disclosed. In at least one embodiment of the invention, a computer program product is disclosed. And in at least one embodiment of the invention, an electronically-readable data medium is disclosed. The dependent claims define preferred and advantageous embodiments of the present invention.

As an embodiment of the present invention, a method is provided for creating a motion correction for PET data which is acquired with the aid of a PET system in a volume segment of a living examination object. An embodiment of the inventive method comprises the following:

Acquisition of MR data within the volume segment with the aid of a magnetic resonance system.

Determination of motion model of a motion (e.g. of the lungs or the heart) within the volume segment, as a function of the acquired MR data. In such cases the motion model delivers a correction specification for the PET data to be acquired, which is acquired during a specific motion state, in order to correct this PET data as a function of the respective motion state of the motion. For this purpose the motion model especially comprises a number of motion fields, which for example have a correction vector for correcting the motion for each pixel of a PET image.

As an embodiment of the present invention, a method is also provided for creation of PET images from PET data which is acquired by way of a PET system in a volume segment of an examination object. In this case a motion within the volume segment is corrected with a motion correction which was created in accordance with at least one embodiment of one of the previously described inventive methods.

Two variants exist for employing embodiments of the inventively created motion correction:

A physiological signal of the examination object is acquired in order to define the current motion state of the examination object as a function of the physiological signal, in order then to carry out the motion correction as a function of the current motion state determined in this way. The physiological signal can for example be acquired with the aid of a respiration strap (for determining the respiration state) or with the aid of an EKG (for determining the heart motion state).

MR data is also acquired within the volume segment simultaneously with the PET data in order to determine the current motion state as a function of this MR data in order then to carry out the motion correction as a function of the current motion state determined in this way. In this case a navigator sequence or a self-navigating sequence can be employed in the MR measurement for acquisition of the MR data.

As part of at least one embodiment of the present invention, a magnetic resonance system is also provided for creating a motion correction for PET data, which is acquired with the aid of the PET system in a volume segment of an examination object. In this case the magnetic resonance system comprises a basic field magnet, a gradient field system, at least one RF transmit/receive antenna, at least one receive coil element and a control device. The control device serves to activate the gradient field system in the at least one RF transmit/receive antenna. Above and beyond this the control device is embodied to receive measurement signals which have been acquired by the at least one RF transmit/receive antenna or by the at least one receive coil element.

As an embodiment of the present invention, a PET system is also provided which has a control unit for activating a positron emission detector of the PET system and an image processing unit for receiving PET data of the predetermined volume segment acquired by the positron emission detector and for creating the PET images from the PET data. An embodiment of the inventive PET system is embodied to correct a movement within the volume segment with an inventively created movement correction.

The inventive PET system can additionally be embodied to acquire a physiological signal of the examination object and to determine the current motion state as a function of the physiological signal, in order to carry out the motion correction as a function of the current motion state.

It is however also possible for an embodiment of the inventive PET system to involve a combined MR/PET system, which is embodied to acquire PET data simultaneously with MR data in the volume segment, in order to determine the current motion state as a function of the acquired MR data.

Inventively it is also possible for the motion model in to be created as a function of MR data which is acquired simultaneously with the PET data. By comparison with the motion models determined beforehand (e.g. the variant with respiration strap) the advantage of a simultaneous PET-MR measurement is that the motion model statistically represents the actual movement during the PET measurement. By contrast a motion model determined beforehand can lead to unusable results if for example the motion behavior of the examination object changes during the measurements. A further advantage of the simultaneous MR-PET measurement is that the actual position of the examination object during acquisition of the PET data and the motion model match exactly.

The advantages of embodiments of the inventive combined MR/PET system essentially also correspond in this case to the advantages of the embodiments of the inventive method for creating PET images, which have previously been explained in detail, so that this explanation will not be repeated here.

An embodiment of the present invention further describes a computer program product, especially a computer program or software which can be loaded into a memory of a programmable controller or a processing unit of a combined MR/PET device or a PET system. With this computer program product, all or various previously described embodiments of the inventive method can be executed when the computer program product is running in a controller or control device of the combined MR/PET device or PET system. In this case the computer program product may possibly need program code/segments, e.g. libraries and auxiliary functions, in order to realize the corresponding embodiment of the method. In other words, the claim directed to the computer program product is especially designed to protect a computer program or software with which the embodiments of the inventive method described above can be executed or which executes this embodiment. In such cases the software can involve a source code (e.g. C++), which still has to be compiled (translated) and linked, or only has to be interpreted, or can involve executable software code which only has to be loaded into the corresponding processing unit to execute it.

Finally, at least one embodiment of the present invention discloses an electronically-readable data medium, e.g. a DVD, a magnetic tape or a USB stick, on which electronically-readable control information, especially software (cf. above), is stored. When this control information (software) is read from the data medium and is stored in a controller or processing unit of a combined MR/PET device or PET system, all inventive embodiments of the previously described method can be carried out.

At least one embodiment of the present invention is especially suited to correction of respiration motions during the creation of PET images. Naturally, embodiments of the present invention are not restricted to this preferred area of application since embodiments of the present invention can also correct heart motions or motions of other organs during the creation of PET images.

BRIEF DESCRIPTION OF THE DRAWINGS

The present invention is described below in detail on the basis of preferred example embodiments which refer to the figures.

FIG. 3 presents a flow plan of an embodiment of an inventive method for creating PET image.

DETAILED DESCRIPTION OF THE EXAMPLE EMBODIMENTS

Figure 1:
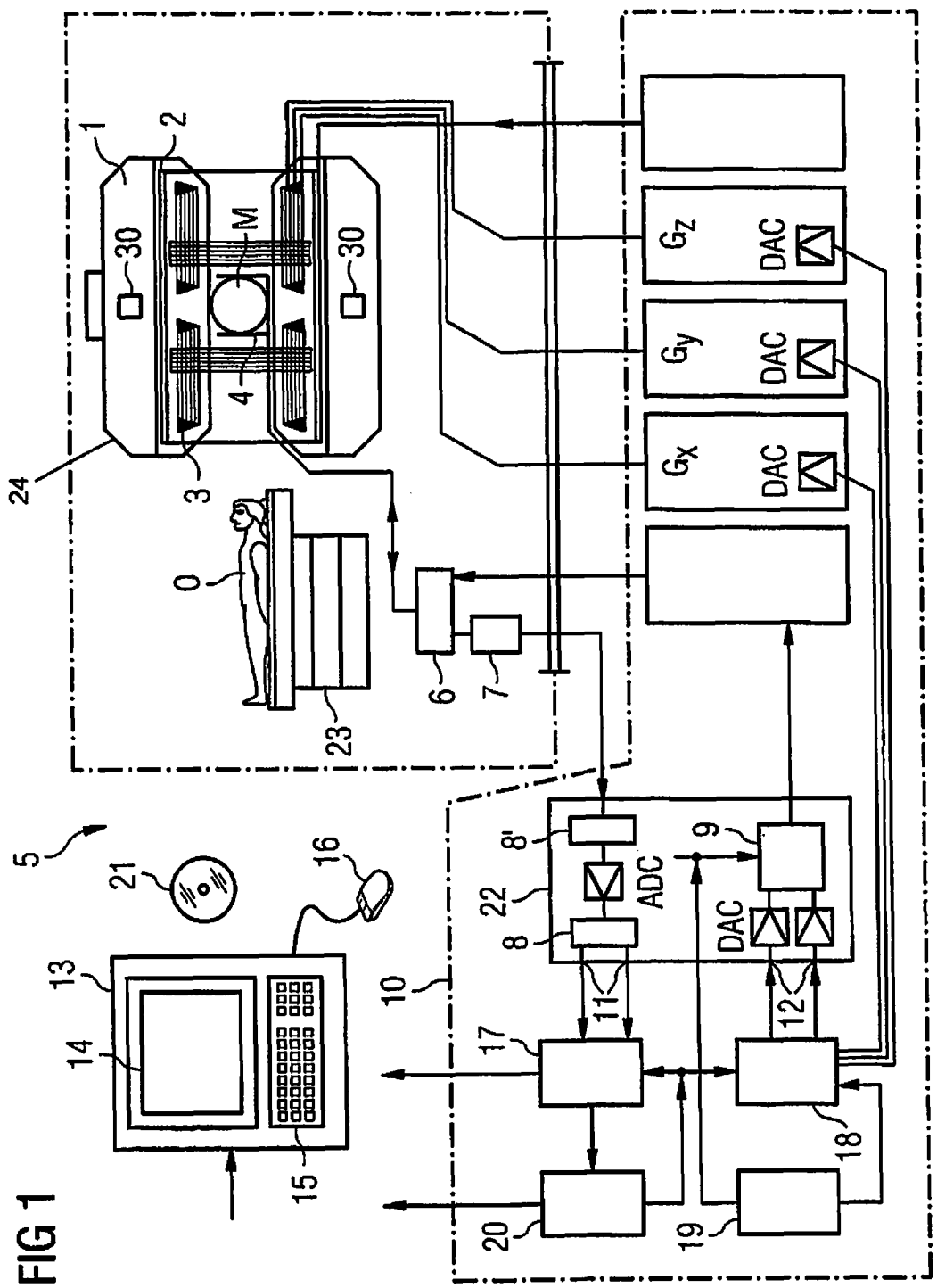
FIG. 1 shows a schematic diagram of an embodiment of an inventive combined MR/PET system.

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

Before discussing example embodiments in more detail, it is noted that some example embodiments are described as processes or methods depicted as flowcharts. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Methods discussed below, some of which are illustrated by the flow charts, may be implemented by hardware, software, firmware, middleware, microcode, hardware description languages, or any combination thereof. When implemented in software, firmware, middleware or microcode, the program code or code segments to perform the necessary tasks will be stored in a machine or computer readable medium such as a storage medium or non-transitory computer readable medium. A processor(s) will perform the necessary tasks.

Specific structural and functional details disclosed herein are merely representative for purposes of describing example embodiments of the present invention. This invention may, however, be embodied in many alternate forms and should not be construed as limited to only the embodiments set forth herein.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

In the following description, illustrative embodiments may be described with reference to acts and symbolic representations of operations (e.g., in the form of flowcharts) that may be implemented as program modules or functional processes include routines, programs, objects, components, data structures, etc., that perform particular tasks or implement particular abstract data types and may be implemented using existing hardware at existing network elements. Such existing hardware may include one or more Central Processing Units (CPUs), digital signal processors (DSPs), application-specific-integrated-circuits, field programmable gate arrays (FPGAs) computers or the like.

Note also that the software implemented aspects of the example embodiments may be typically encoded on some form of program storage medium or implemented over some type of transmission medium. The program storage medium (e.g., non-transitory storage medium) may be magnetic (e.g., a floppy disk or a hard drive) or optical (e.g., a compact disk read only memory, or "CD ROM"), and may be read only or random access. Similarly, the transmission medium may be twisted wire pairs, coaxial cable, optical fiber, or some other suitable transmission medium known to the art. The example embodiments not limited by these aspects of any given implementation.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

As an embodiment of the present invention, a method is provided for creating a motion correction for PET data which is acquired with the aid of a PET system in a volume segment of a living examination object. An embodiment of the inventive method comprises the following:

Acquisition of MR data within the volume segment with the aid of a magnetic resonance system.

Determination of motion model of a motion (e.g. of the lungs or the heart) within the volume segment, as a function of the acquired MR data. In such cases the motion model delivers a correction specification for the PET data to be acquired, which is acquired during a specific motion state, in order to correct this PET data as a function of the respective motion state of the motion. For this purpose the motion model especially comprises a number of motion fields, which for example have a correction vector for correcting the motion for each pixel of a PET image.

In such cases, during acquisition of the MR data, specific MR raw data is acquired in the center of the k-space or specific MR raw data is acquired on a straight-line segment which passes through the center of the k-space. This specific MR raw data is converted by a mathematical function into (precisely) one value, as a function of which the respective motion state is then determined.

In other words the MR raw data determined is not converted into MR image data in order to determine the value by way of the mathematical function, as a function of which the respective motion state is then determined. In that the value corresponding to the motion state to be determined is determined from the MR raw data solely by a simple mathematical function, the respective current motion state can advantageously be determined very simply and very quickly.

It should be pointed out that the MR raw data, for the case in which only the MR raw data of the k-space center is used, only includes precisely one complex number, from which the respective motion state is then derived.

The mathematical function can correspond to an averaging of the MR raw data determined. I.e. the value, as a function of which the respective motion state is established, corresponds to the average value of the MR raw data acquired in the center of the k-space or along the straight-line segment through the k-space center.

For the respiration state (motion state of the lungs) it is true to say for example that the value (average value) is all the smaller, the more air that there is within the lungs. On the other hand, for the movement state of the heart for example, it is true to say that the value (average value) becomes smaller when parts of the heart move out of the volume segment, and that the value becomes larger when parts of the heart move into the volume segment. In other words the value is all the greater in relation to the heart motion, the greater is the proportion of the heart which is located within the volume segment.

In accordance with an inventive embodiment, the acquisition of the MR data includes an acquisition of MR data along a number of straight-line segments which run in planes (layers) parallel to one another. In such cases the MR data for each of these layers is acquired with the aid of a radial sampling scheme. A radial sampling scheme is to be understood as the straight-line segments in the respective layer extending from a first edge point of the k-space through the center of the layer to a second edge point of the k-space lying opposite the first edge point.

In such cases one of these planes or layers in particular passes through the k-space center so that the MR raw data determined, from which the current motion state is derived, is acquired in this layer.

Looking at a specific layer, the straight-line segments in this layer will especially be completely sampled one after the other in a predefined sequence. In this case an angle which lies between a straight-line segment and a straight-line segment following said segment in accordance with the sequence is the so-called golden angle. As regards the golden angle four variants exist. If a full circle (360°) is divided with straight-line segments, then this can be done with the large golden angle (222.5°) or with the small golden angle (137.5°). If the semicircle (180°) is divided with straight-line segments, this can be done with the (half) large golden angle) ((111.25°) all with the (half) small golden angle (68.75°). It should be pointed out that in all variants (even with the variants related to the semicircle) the straight-line segment defined with the golden angle measures through the entire k-space (i.e. not only the semicircle).

It is preferred that, in each plane or layer, the straight-line segment with a location the same in all layers is first sampled, before in each layer the following respective straight-line segments in accordance with the sequence (which likewise have the same location in all layers) are sampled etc. It is however also possible for all straight-line segments of a layer to be sampled first in the said sequence before the straight-line segments of the next layer are sampled etc.

According to at least one embodiment of the invention it is however also possible for the MR data to be acquired in the form of a three-dimensional radial data acquisition. In such cases the three-dimensional k-space center is sampled along the straight-line segments or spokes which extend from a k-space boundary through the k-space center to the opposite k-space boundary.

While it is sufficient, for determining the motion state, to only acquire the MR raw data of the k-space point in the k-space center, for creating the motion model (almost) the entire k-space must be sampled for each motion state.

In accordance with a first preferred embodiment of the invention, as a function of the MR data which is acquired for each motion state, an individual attenuation map is created for each of the selected motion states. In this case the PET images are reconstructed from the PET data which is acquired during the respective motion state with the aid of the individually-created attenuation map for the motion state. The PET images corrected in this way are then transformed with the aid of the motion model into the same predetermined motion state (reference motion state).

The PET images corrected and transformed in this way can then be summed or collected together in order to create the final PET image.

To create the individual attenuation map, a pre-measurement is preferably carried out in order to create a (reference) attenuation map for a perfect motion state (mostly the reference motion state). The respective individual attenuation map is then derived from this reference attenuation map with the aid of the motion model.

In other words, the attenuation map is adapted on the basis of the motion fields of the respective motion model for the respective motion state (respiration state). The attenuation-corrected PET images of the different motion states reconstructed with these attenuation maps can then be transformed with the aid of the motion fields to a previously defined motion state (the predetermined motion state) and finally summed.

In accordance with a second preferred embodiment of the invention, the PET data (as PET data) is transformed with the aid of the motion model into the same predetermined motion state. Depending on the MR data which is acquired for this predetermined motion state, an attenuation map is created and all PET data (from the different motion states) is corrected with the aid of this one attenuation map.

To put it in another way, in the second embodiment, the PET raw data is already transformed (and collected) with the aid of the motion fields of the motion model into the predetermined motion state. The actual PET image is then reconstructed with the attenuation map from the PET data corrected in this way. In the second embodiment the motion information (from the motion model) can be integrated directly into the system matrix which is employed for PET image reconstruction.

In accordance with a third inventive embodiment, the movement correction and the attenuation correction are integrated into a specific reconstruction which reconstructs the PET image data from the PET raw data. To put it another way, on the one hand the motion correction is integrated into the specific reconstruction, so that during the reconstruction of the PET image data from the PET raw data the motion is corrected quasi-implicitly with the aid of the motion model. On the other hand the attenuation correction (e.g. with the aid of the attenuation map) is also integrated into the specific reconstruction. With the third embodiment too, the motion information (from the motion model) can be integrated directly into the system matrix which is employed for PET image reconstruction.

As an embodiment of the present invention, a method is also provided for creation of PET images from PET data which is acquired by way of a PET system in a volume segment of an examination object. In this case a motion within the volume segment is corrected with a motion correction which was created in accordance with at least one embodiment of one of the previously described inventive methods.

Two variants exist for employing embodiments of the inventively created motion correction:

A physiological signal of the examination object is acquired in order to define the current motion state of the examination object as a function of the physiological signal, in order then to carry out the motion correction as a function of the current motion state determined in this way. The physiological signal can for example be acquired with the aid of a respiration strap (for determining the respiration state) or with the aid of an EKG (for determining the heart motion state).

MR data is also acquired within the volume segment simultaneously with the PET data in order to determine the current motion state as a function of this MR data in order then to carry out the motion correction as a function of the current motion state determined in this way. In this case a navigator sequence or a self-navigating sequence can be employed in the MR measurement for acquisition of the MR data.

When the motion state is acquired on the basis of the physiological signal, this physiological signal is especially also acquired during the inventive creation of the motion correction, so that almost during the creation of the motion correction a correlation is established between the physiological signal and the motion state determined during the creation of the motion correction. On the basis of this correlation the corresponding motion state can then be established during acquisition of the PET data with the aid of the currently acquired physiological signal.

If on the other hand the motion state is determined on the basis of the simultaneously acquired MR data, it is advantageous if, in accordance with the invention, the motion model is also created on the basis of this MR data. In addition to the advantage that no additional device is required for acquiring the physiological signal, this variant offers the additional advantage that current changes in position of organs in the examination object are reflected in the acquired MR data (and thus in the motion model). On the other hand only an indirect indicator for a corresponding organ motion can ever be established by the acquisition of a physiological signal.

In other words the motion correction of the PET data is carried out in this variant on the basis of a motion model which is created on the basis of the MR data which is acquired simultaneously with the PET data.

Embodiments of the present invention make it possible for all events of a PET acquisition to be used, whereby the image quality is improved compared to a triggered or gated measurement in which the PET data not fitting in with the respective motion state is discarded. By comparison with a conventional PET reconstruction without determination of the motion state, motion artifacts are markedly reduced and the quantitative information is improved in the inventively created PET images.

As part of at least one embodiment of the present invention, a magnetic resonance system is also provided for creating a motion correction for PET data, which is acquired with the aid of the PET system in a volume segment of an examination object. In this case the magnetic resonance system comprises a basic field magnet, a gradient field system, at least one RF transmit/receive antenna, at least one receive coil element and a control device. The control device serves to activate the gradient field system in the at least one RF transmit/receive antenna. Above and beyond this the control device is embodied to receive measurement signals which have been acquired by the at least one RF transmit/receive antenna or by the at least one receive coil element.

The magnetic resonance system is embodied to acquire MR data in a predetermined volume segment and to determine, as a function of this MR data, a motion model of a motion within the volume segment. In this case the motion model, as a function of a respective motion state of the motion, provides a correction specification for the PET data which is acquired during the respective motion state.

The magnetic resonance system is additionally embodied, during the acquisition of the MR data, to acquire specific MR raw data in the center of the k-space, or along a straight-line segment which passes through the center of the k-space. The magnetic resonance system converts MR raw data determined in this way by way of its control device through a mathematical function into a value and determines the respective motion state as a function of this value.

The advantages of embodiments of the inventive magnetic resonance system correspond to the advantages of the embodiments of the inventive method for creating a motion correction for the PET data which have been explained in detail previously, so that this explanation will not be repeated here.

As an embodiment of the present invention, a PET system is also provided which has a control unit for activating a positron emission detector of the PET system and an image processing unit for receiving PET data of the predetermined volume segment acquired by the positron emission detector and for creating the PET images from the PET data. An embodiment of the inventive PET system is embodied to correct a movement within the volume segment with an inventively created movement correction.

The inventive PET system can additionally be embodied to acquire a physiological signal of the examination object and to determine the current motion state as a function of the physiological signal, in order to carry out the motion correction as a function of the current motion state.

It is however also possible for an embodiment of the inventive PET system to involve a combined MR/PET system, which is embodied to acquire PET data simultaneously with MR data in the volume segment, in order to determine the current motion state as a function of the acquired MR data.

Inventively it is also possible for the motion model in to be created as a function of MR data which is acquired simultaneously with the PET data. By comparison with the motion models determined beforehand (e.g. the variant with respiration strap) the advantage of a simultaneous PET-MR measurement is that the motion model statistically represents the actual movement during the PET measurement. By contrast a motion model determined beforehand can lead to unusable results if for example the motion behavior of the examination object changes during the measurements. A further advantage of the simultaneous MR-PET measurement is that the actual position of the examination object during acquisition of the PET data and the motion model match exactly.

The advantages of embodiments of the inventive combined MR/PET system essentially also correspond in this case to the advantages of the embodiments of the inventive method for creating PET images, which have previously been explained in detail, so that this explanation will not be repeated here.

An embodiment of the present invention further describes a computer program product, especially a computer program or software which can be loaded into a memory of a programmable controller or a processing unit of a combined MR/PET device or a PET system. With this computer program product, all or various previously described embodiments of the inventive method can be executed when the computer program product is running in a controller or control device of the combined MR/PET device or PET system. In this case the computer program product may possibly need program code/segments, e.g. libraries and auxiliary functions, in order to realize the corresponding embodiment of the method. In other words, the claim directed to the computer program product is especially designed to protect a computer program or software with which the embodiments of the inventive method described above can be executed or which executes this embodiment. In such cases the software can involve a source code (e.g. C++), which still has to be compiled (translated) and linked, or only has to be interpreted, or can involve executable software code which only has to be loaded into the corresponding processing unit to execute it.

Finally, at least one embodiment of the present invention discloses an electronically-readable data medium, e.g. a DVD, a magnetic tape or a USB stick, on which electronically-readable control information, especially software (cf. above), is stored. When this control information (software) is read from the data medium and is stored in a controller or processing unit of a combined MR/PET device or PET system, all inventive embodiments of the previously described method can be carried out.

At least one embodiment of the present invention is especially suited to correction of respiration motions during the creation of PET images. Naturally, embodiments of the present invention are not restricted to this preferred area of application since embodiments of the present invention can also correct heart motions or motions of other organs during the creation of PET images.

FIG. 1 shows a schematic diagram of a combined MR/PET device 5 which includes a positron emission detector 30 and a magnetic resonance system 24. In this device a basic field magnet 1 of the magnetic resonance system 24 creates a strong magnetic field constant over time for polarization or alignment of the nuclear spin in an examination area of an object O, such as a part of a human body to be examined for example, which is pushed into the magnetic resonance system 24, lying on a table 23, for creation of an image. The high homogeneity of the basic magnetic field required for the nuclear magnetic resonance measurement is defined in a typically spherical measurement volume M in which the parts of the human body to be examined are disposed for acquisition of the MR data. To support the homogeneity requirements and especially to eliminate temporally-invariable influences, what are referred to as shims made of ferromagnetic material are attached at a suitable point. Temporally-variable influences are eliminated by shim coils.

A cylindrical gradient coil system 3 is used in the basic field magnet 1, which includes three part windings. Each part winding is supplied by a corresponding amplifier with current for creating a linear (also temporally variable) gradient field in the respective direction of a Cartesian coordinate system. The first part winding of the gradient field system 3 in this case creates a gradient Gx in the x-direction, the second part winding creates a gradient Gy in the y-direction and the third part winding creates a gradient Gz in the z-direction. The amplifier includes a Digital-Analog Converter (DAC), which is activated by a sequence controller 18 for the creation of gradient pulses at the correct time.

Located within the gradient field system 3 is one (or more) radio-frequency antennas 4, which convert the radio-frequency pulses emitted by a radio-frequency power amplifier into a magnetic alternating field for exciting the nuclei and aligning the nuclear spin of the object O to be examined or of the area to be examined of the object O. Each radio frequency antenna 4 includes one or more RF transmit coils and one or more RF receive coils in the form of a ring-shaped, preferably linear or matrix-shaped arrangement of component coils. From the RF receive coils of a radio-frequency antenna 4 the alternating field emanating from the preceding nuclear resonance, i.e. as a rule the nuclear resonance echo signals caused by a pulse sequence or one or more radio-frequency pulses and one or more gradient pulses, is converted into a voltage (measurement signal), which is fed by an amplifier 7 to a radio-frequency receive channel 8 of a radio-frequency system 22. The radio-frequency system 22 further comprises a transmit channel 9 in which the radio-frequency pulses for the excitation of the magnetic nuclear resonance are created. In such cases the respective radio-frequency pulses are represented digitally in the sequence control 18 as a sequence of complex numbers on the basis of a pulse sequence predetermined by a system processor 20. This numerical sequence is supplied as a real part and as an imaginary part via an input 12 in each case to a Digital-Analog Converter (DAC) in the radio-frequency system 22 and supplied from this to the transmit channel 9. In the transmit channel 9 the pulse sequences are modulated up to a radio-frequency carrier signal of which the basic frequency corresponds to the resonance frequency of the nuclear spin in the measurement volume.

The switchover from transmit to receive mode is made via a transmit-receive switch 6. The RF transmit coils of the radio frequency antennas 4 transmit the radio frequency pulses for exciting the nuclear spin into the measurement volume M and resulting echo signals are sampled via the RF receive coils. The nuclear resonance signals obtained accordingly are demodulated in the receive channel 8' (first demodulator) of the radio-frequency system 22 in a phase-sensitive manner to an intermediate frequency and are digitized in the analog-digital converter (ADC). This signal is again demodulated to the frequency zero. The demodulation to the frequency zero and the separation into real and imaginary part takes place after the digitization in the digital domain in a second demodulator 8. From the measurement data obtained in this way, a PET image (and under some circumstances also an MR image) are reconstructed by an image processor 17. The measurement data, the image data and the control programs are managed via the system processor 20. On the basis of a specification with control programs, the sequence control 18 checks the creation of the respective desired pulse sequences and the corresponding sampling of the k-space. In particular the sequence control 18 in such cases controls the timely switching of the gradients, the transmission of the radio-frequency pulses with defined phase amplitude and also the receiving of the nuclear resonance signals. The time base for the radio-frequency system 22 and the sequence control 18 is provided by a synthesizer 19.

As has already been explained previously, the MR/PET device 5 includes a positron emission detector 30 which is mostly embodied in the shape of a ring. The tracers used for PET are marked with a positron emitter. During the decay of this positron emitter in the tissue of the patient O two γ-quanta are created in the vicinity of the location of the corresponding positron emission by an annihilation, which fly away from each other in opposite directions. If these two γ-quanta are measured by two opposite detector elements of the positron emission detector 30 within a predetermined coincidence time interval, the location of the annihilation can be fixed to a position on the connecting line between these two detector elements.

The PET data is acquired with the positron emission detector 30, from which the PET image is then created in the image processor 17. The PET image can be combined in the image processor with an MR image in order to create a combined MR/PET image.

The corresponding control programs for creating the MR images, PET images and combined MR/PET images, which are stored for example on a DVD 21, are selected, and the created images are also displayed via a terminal 13 which comprises a keyboard 15, a mouse 16 and a screen 14.

Figure 2:
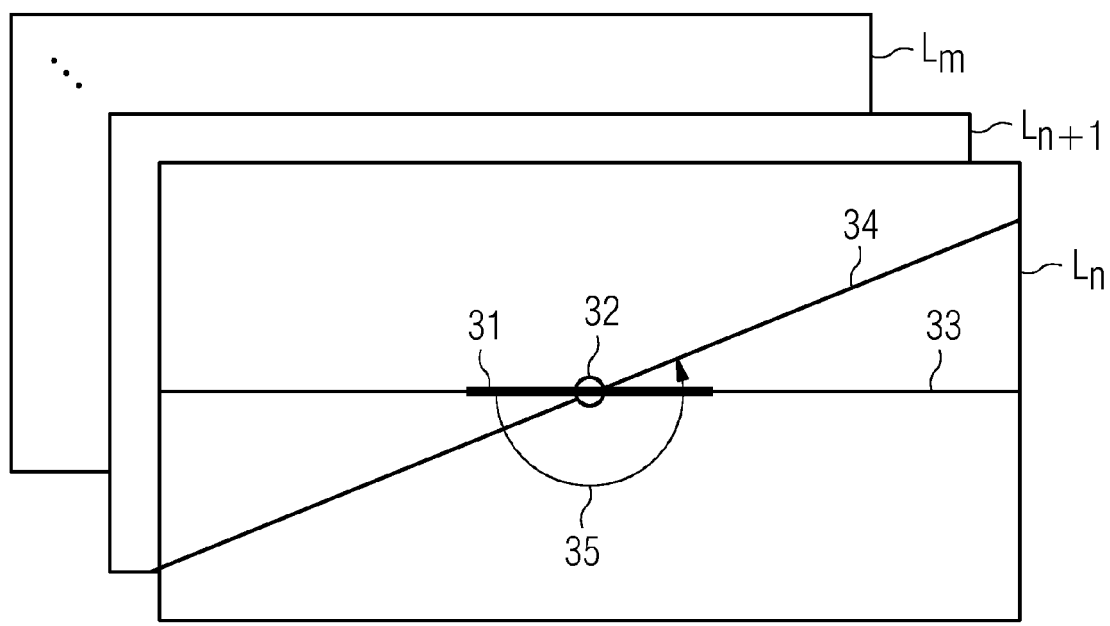
FIG. 2 shows schematically how the k-space can be sampled radially with a number of layers in accordance with an embodiment of the invention.

FIG. 2 shows schematically how the k-space is sampled in layers with the aid of the stack-of-stars sampling scheme. To this end a number of layers $L_1$-$L_m$ (only $L_n$-$L_m$ are shown in FIG. 2) are sampled radially.

Radial sampling in this case is to be understood as the respective layer $L_n$-$L_m$ being sampled along spokes 33, 34 which pass within the layer $L_n$-$L_m$ from an edge of the layer Ln-Lm through the center 32 of the layer $L_n$-$L_m$ in a straight line to the opposite edge of the layer $L_n$-$L_m$ In this case the spoke 33 currently being sampled and the spoke 34 subsequently sampled enclose an angle 35 which corresponds to the golden angle.

The layer identified by the reference character Ln passes through the k-space center 32, so that the center of this layer Ln corresponds to the k-space center 32 (of the three-dimensional k-space). In order to acquire the current movement state which the examination object has while the MR data is being acquired in the k-space, the MR raw data is acquired along a straight-line segment 31 which passes through the k-space center 32, and averaged. The current motion state can then be acquired on the basis of the average value of this MR raw data.

It should be pointed out that the MR raw data on the basis of which the current motion state is determined especially represents a subset of that MR raw data which is acquired during sampling of the k-space for creating the movement model.

FIG. 3 shows a schematic of a flow plan of an an embodiment of an inventive method for creation of PET images.

In a first step S1, MR data is acquired in a volume segment of an examination object. Depending on the MR raw data which is also acquired in step S1 along a straight-line segment 31 (see FIG. 2) through the k-space center, in step S2 the current movement state of the examination object is determined.

The steps S1 and S2 will execute consecutively until such time as the MR data in the volume segment has been acquired over at least one motion period, so that in the following step S3 a motion model can be created. This motion model is created with the aid of what is known as non-rigid registration. To do this MR images are created in each case from the MR data for the various motion states, in which respective specific objects (for example the lungs) are localized and which are then registered non-rigidly (i.e. elastically) with the respective corresponding object of the next MR image in time (i.e. brought into a best-possible match).

The motion model created or determined in step S3 includes a number of motion fields which allow PET images of different motion states (e.g. respiration states) to be transformed into one reference motion state. In order to now create a PET image with the motion model determined in step S3, on the one hand PET data is acquired in step S6 and on the other hand simultaneously (with the acquisition of the PET data) the current motion state is acquired in step S5.

In step S7 the PET data is corrected with the aid of the motion model as a function of the current motion state. The steps S5 to S7 will be run often enough for a sufficient volume of PET data to have been acquired so that then finally, in step S8, a PET image can be created from the corrected PET data.

In other words the detected events (PET data) will be classified into various motion states with the aid of the motion state acquired in step S5 (e.g. respiration signals). The motion can subsequently be corrected in the image space (i.e. after PET images have been reconstructed from the PET data) or also in the raw data space (i.e. by a correction of the PET data without prior reconstruction into PET images).

It should be pointed out that steps S1 and S6 can also be carried out simultaneously, so that the MR data and the PET data is acquired simultaneously. In this case the current motion state S5 is acquired as a rule with the aid of the MR data.

The patent claims filed with the application are formulation proposals without prejudice for obtaining more extensive patent protection. The applicant reserves the right to claim even further combinations of features previously disclosed only in the description and/or drawings.

The example embodiment or each example embodiment should not be understood as a restriction of the invention. Rather, numerous variations and modifications are possible in the context of the present disclosure, in particular those variants and combinations which can be inferred by the person skilled in the art with regard to achieving the object for example by combination or modification of individual features or elements or method steps that are described in connection with the general or specific part of the description and are contained in the claims and/or the drawings, and, by way of combinable features, lead to a new subject matter or to new method steps or sequences of method steps, including insofar as they concern production, testing and operating methods.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program, tangible computer readable medium and tangible computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a tangible computer readable medium and is adapted to perform any one of the aforementioned methods when run on a computer device (a device including a processor). Thus, the tangible storage medium or tangible computer readable medium, is adapted to store information and is adapted to interact with a data processing facility or computer device to execute the program of any of the above mentioned embodiments and/or to perform the method of any of the above mentioned embodiments.

The tangible computer readable medium or tangible storage medium may be a built-in medium installed inside a computer device main body or a removable tangible medium arranged so that it can be separated from the computer device main body. Examples of the built-in tangible medium include, but are not limited to, rewriteable non-volatile memories, such as ROMs and flash memories, and hard disks. Examples of the removable tangible medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Although the invention has been illustrated and described in detail on the basis of the preferred example embodiment, the invention is not limited by the disclosed examples and other variations can be derived herefrom by the person skilled in the art, without departing from the scope of protection of the invention.

What is claimed is:

1. A method for generating at least one positron emission tomography (PET) image based on a motion correction for PET data acquired by a PET system from a volume segment of an examination object, the method comprising:
    acquiring magnetic resonance (MR) data within the volume segment via a magnetic resonance system, the acquiring including,
        acquiring particular MR data along straight-line segments that pass through a center of a k-space and are disposed in layers parallel to one another, an angle between a first straight-line segment and a subsequent straight-line segment corresponding to a golden angle, each of the straight-line segments intersects with an axis which is at a right angle to each layer and passes through the center of the k-space, the acquiring the particular MR data acquires the particular MR data in each respective layer along straight-line segments having a same position in the layers, respectively, before acquiring the particular MR data along the subsequent straight-line segment;
    obtaining the PET data;
    determining a motion model of a motion within the volume segment as a function of the MR data, the motion model providing a correction specification for PET data acquired during a respective motion state as a function of the respective motion state of the motion, the determining the motion model including converting only the particular MR data by a mathematical function into one value and the respective motion state is determined as a function of the one value, only the particular MR data passing through the center of the k-space;
    correcting the PET data using the motion model to generate the at least one PET image; and
    generating the at least one PET image using the corrected PET data.

2. The method of claim 1, wherein the mathematical function corresponds to an averaging of the particular MR data such that the value corresponds to an average value of the particular MR data.

3. A non-transitory computer readable medium including program code segments, when executed by a control device of a PET system, an MR system or a combined MR/PET device, cause the control device to perform the method of claim 2.

4. The method of claim 1, wherein the correcting includes,
    generating an individual attenuation map as a function of the MR data for each respective motion state, the correcting of the PET data includes correcting the PET data acquired during the respective motion state with the individual attenuation map corresponding to the respective motion state; and
    transforming the corrected PET data with the motion model into a same selected motion state.

5. The method of claim 1, wherein the correcting includes,
    reconstructing the PET data by integrating the motion correction by way of the motion model and an attenuation correction.

6. The method of claim 1, further comprising:
    acquiring a physiological signal of the examination object, and the correcting includes,
    identifying a current motion state as a function of the physiological signal and performing the motion correction as a function of the current motion state.

7. The method of claim 1, wherein the acquiring the MR data and the obtaining the PET data are performed simultaneously, and the correcting includes, identifying a current motion state as a function of the MR data and performing motion correction of the PET data as a function of the current motion state.

8. A combined magnetic resonance (MR)/positron emission tomography (PET) system for creating PET images in a volume segment of an examination object, the combined MR/PET system comprising:
 a control unit configured to activate a positron emission detector of the combined MR/PET system and receive measurement signals accepted by at least one receive coil element of the combined MR/PET system; and
 an image processing unit configured to receive PET data of a volume segment acquired by the positron emission detector, configured to create the PET images from the PET data, and combine the PET images with MR images from MR data based on the measurement signals, wherein the combined MR/PET system is configured to perform the method of claim 1.

9. A non-transitory computer readable medium storing computer readable instructions that, when executed by a control device of a PET system, an MR system or a combined MR/PET device, cause the control device to perform the method of claim 1.

10. A magnetic resonance (MR) system for creating a motion correction for positron emission tomography (PET) data acquired by a PET system from a volume segment of an examination object, the magnetic resonance system comprising:
 a basic field magnet;
 a gradient field system;
 at least one radio frequency (RF) antenna;
 at least one receive coil element; and
 a control device configured to activate the gradient field system and the at least one RF antenna, configured to receive measurement signals accepted by the at least one receive coil element and configured to evaluate the measurement signals and create MR data of the volume segment, wherein
 the control device is configured to determine a motion model of a motion within the volume segment as a function of the MR data, wherein the motion model provides a correction specification for PET data acquired during a respective motion state as a function of the respective motion state of the motion, wherein the control device is configured to acquire particular MR data of the created MR data along straight-line segments which pass through a center of a k-space and are disposed in layers parallel to one another in order to convert only the particular MR data by a mathematical function into one value and to determine the respective motion state as a function of the one value, only the particular MR data passing through the center of the k-space, an angle between a first straight-line segment and a subsequent straight-line segment corresponding to a golden angle, each of the straight-line segments intersects with an axis which is at a right angle to each layer and passes through the center of the k-space, and the control device is configured to acquire the particular MR data by acquiring the particular MR data in each respective layer along straight-line segments having a same position in the layers, respectively, before acquiring the particular MR data along the subsequent straight-line segment.

11. A combined positron emission tomography (PET) and magnetic resonance (MR) system for creating at least one PET image in a volume segment of an examination object, the combined PET and MR system comprising:
 a positron emission detector;
 a control unit configured to activate the positron emission detector of the PET system; and
 an image processing unit configured to receive PET data of a volume segment acquired by the positron emission detector and configured to create the PET images from the PET data, wherein the combined PET and MR system is configured to correct a motion within the volume segment with motion correction, created by,
  acquiring MR data within the volume segment, the acquiring including, acquiring particular MR data along straight-line segments that pass through a center of a k-space and are disposed in layers parallel to one another, an angle between a first straight-line segment and a subsequent straight-line segment corresponding to a golden angle, each of the straight-line segments intersects with an axis which is at a right angle to each layer and passes through the center of the k-space, the acquiring the particular MR data in each acquires the particular MR data in each respective layer along straight-line segments having a same position in the layers, respectively, before acquiring the particular MR data along the subsequent straight-line segment, and
  determining a motion model of a motion within the volume segment as a function of the MR data, wherein the motion model provides, as a function of a respective motion state of the motion, a correction specification for PET data acquired during the respective motion state, wherein, during the acquiring of the MR data, only the particular MR data is converted by a mathematical function into one value and the respective motion state is determined as a function of the one value, and only the particular MR data passes through the center of the k-space,
 the image processing unit being further configured to correct the PET data to generate the at least one PET image.

12. The combined PET and MR system of claim 11, wherein the combined PET and MR system is configured to,
 acquire a physiological signal of the examination object, and
 determine a current motion state as a function of the physiological signal in order to carry out the motion correction as a function of the current motion state.

* * * * *